United States Patent [19]
Runyan et al.

[11] Patent Number: 5,274,438
[45] Date of Patent: Dec. 28, 1993

[54] CAN-MEASURING DENSITOMER

[75] Inventors: Steven Runyan, Los Altos Hills, Calif.; James R. Cox, Richardson, Tex.

[73] Assignee: Graphics Microsystems, Inc., Sunnyvale, Calif.

[21] Appl. No.: 763,980

[22] Filed: Sep. 23, 1991

[51] Int. Cl.⁵ .................................. G01J 3/46
[52] U.S. Cl. ........................ 356/402; 250/223 B
[58] Field of Search .................. 356/402–411, 356/407, 418, 419, 425, 443, 444, 446; 364/526; 250/223 B, 222.1

[56] References Cited

U.S. PATENT DOCUMENTS 4,090,243  5/1978  Kotera et al. .............. 356/402
5,073,028 12/1991  Bowden et al. ............ 356/402

OTHER PUBLICATIONS

Sales brochure for Hammamatsu Position-Sensitive Detectors, Oct. 1988.
Sales brochure for UDT 431 X-Y Optical Position Indicator.
Sales brochure for OP-EYE Optical Position Indicator.
Sales brochure for Reticon Image Sensing Products, 1981.
Sales brochure for Cosar Auto Smart Desitometer.
Introduction for Cosar Auto Smart Densitometer.

*Primary Examiner*—Vincent P. McGraw
*Assistant Examiner*—K. P. Hantis
*Attorney, Agent, or Firm*—Limbach & Limbach

[57] ABSTRACT

A system for measuring the color quality of rounded objects is disclosed. A stand has a mandrel for holding the object in a fixed position. Preferably, the mandrel includes an expandable bladder mounted for rotation on an axle. The stand has a reflectometer coupled thereto in such a way as to permit angular movement of the densitometer in a fixed plane. The can is clamped in a fixed position between the holding means and the densitometer such that the densitometer is in a fixed radial orientation relative to the surface of the object. Different points on the surface of the object may be measured by rotating and translating the object and/or the reflectometer. Rotational and translation control of positioning can be performed automatically.

27 Claims, 4 Drawing Sheets

CAN-MEASURING DENSITOMER

BACKGROUND

1. Field of the Invention

The present invention relates to color quality measurement, and more particularly, to a system that can measure the color quality of a rounded surface, such as a two-piece can.

2. Discussion of the Prior Art

A reflectometer is a well known optical measurement instrument that is used for quality control in color printing production processes. The most common use of a reflectometer is to measure ink on paper to control a printing process, although reflectometers are also used to measure photographic prints and other images on various substrates such as paper, plastic and metal, in order to monitor and control the production of the images or to test the production equipment. There are a number of specific types of reflectometers, including reflection densitometers, reflection spectrophotometers, colorimeters, and glossmeters, all of which operate according to the same general principle.

In general, a reflectometer directs a beam of light having a known color quality, i.e., a balance of red, green and blue light in conformance with ANSI/ISO standards, at a printed sample. By using a filtration system, the reflectometer then measures the amount of light which is reflected from the surface of the sample and generates an output signal which is indicative of the reflectance of the sample. The color density of the sample may then be readily determined, since density is the inverse logarithm of reflectance.

Illumination and measurement systems of the type employed in reflectometers are commonly referenced to an axis which is perpendicular to the sample. For example, according to accepted standards for densitometers, the illumination angle is either 45° or 0° degrees, and the measurement angle is then 0° or 45°, respectively. It is then assumed that the light absorbed by the sample is the difference between the incident light and the reflected light. The sample color density can then be calculated according to an accepted logarithmic relationship.

Presently, reflectometers are used to take color quality measurements of flat samples, such as printed lithographed sheets or exposed films. However, visual inspection is used for rounded surfaces, such as plastic or metal containers, and in particular, on a two-piece can of the type used for beer and soda cans. This is due to the difficulty in maintaining accurate illumination and measurement angles when working with rounded surfaces.

Thus, it would be desirable to have a device that could accurately measure the color quality of a set of measurement points on a sample having rounded surfaces, such as a two-piece can.

SUMMARY OF THE INVENTION

A method and apparatus are disclosed for measuring the color quality of printed matter on the rounded surface of an object. In the preferred embodiment, a method and apparatus for examining a two-piece can is described. A stand includes holding means for holding the can in a fixed position. In one embodiment, the holding means comprises a rotatable mandrel having an expandable bladder mounted on an axle. The stand further includes a reflectometer flexibly coupled to the stand in such a way as to permit angular movement of the reflectometer in a fixed plane. Clamping means are provided for securing the can in a fixed position between the holding means and the reflectometer such that, when the clamping means is engaged, the reflectometer is in a fixed radial orientation relative to the surface of the object. In one embodiment, means are provided for translating the reflectometer relative to the surface of the can. Thus, to obtain a series of measurement points at different locations on the surface of the can, the can may be rotated manually on the mandrel and the clamping means engaged.

In operation, the can is placed on the holding means and the reflectometer is flexed toward the surface of the can. The clamping means engages as the reflectometer reaches a predetermined radial orientation relative to the surface. At substantially the same time, the reflectometer is activated so that a measurement of the color quality of a preselected point on the surface of the can may be obtained.

In the various embodiments, different points on the surface of the can may be examined by rotating and translating the can and/or the densitometer. Further, such control can be performed automatically, for example, by a computerized control system.

A better understanding of the features and advantages of the present invention will be obtained by reference to the following detailed description of the invention and accompanying drawings which set forth an illustrative embodiment in which the principles of the invention are utilized.

BRIEF DESCRIPTION OF THE DRAWINGS

FIG. 5b is a sectional plan view taken across section 5b–5b of FIG. 5a.

DETAILED DESCRIPTION OF THE INVENTION

The present invention is described with reference to a standard two-piece aluminum can of the type commonly used as a beer or soda pop container. It should be appreciated that the use of a two-piece can to describe the present invention is intended to be illustrative only, as the present invention has application for the measurement of any rounded surface to which colored printed matter has been applied. Further, while a reflection densitometer is described as the measurement device, it is intended that any type of measurement device, optical or otherwise, be within the scope and spirit of the present invention.

A two-piece can of the type used as a beer or soda pop container is a simple cylinder measuring substantially 5 inches in length and 2.25 inches in diameter. Printed matter is applied to the surface of the can after the can has been formed, and then a top is put on the can. The quality of the printed matter may be examined prior to affixing the can top.

Figure 1:
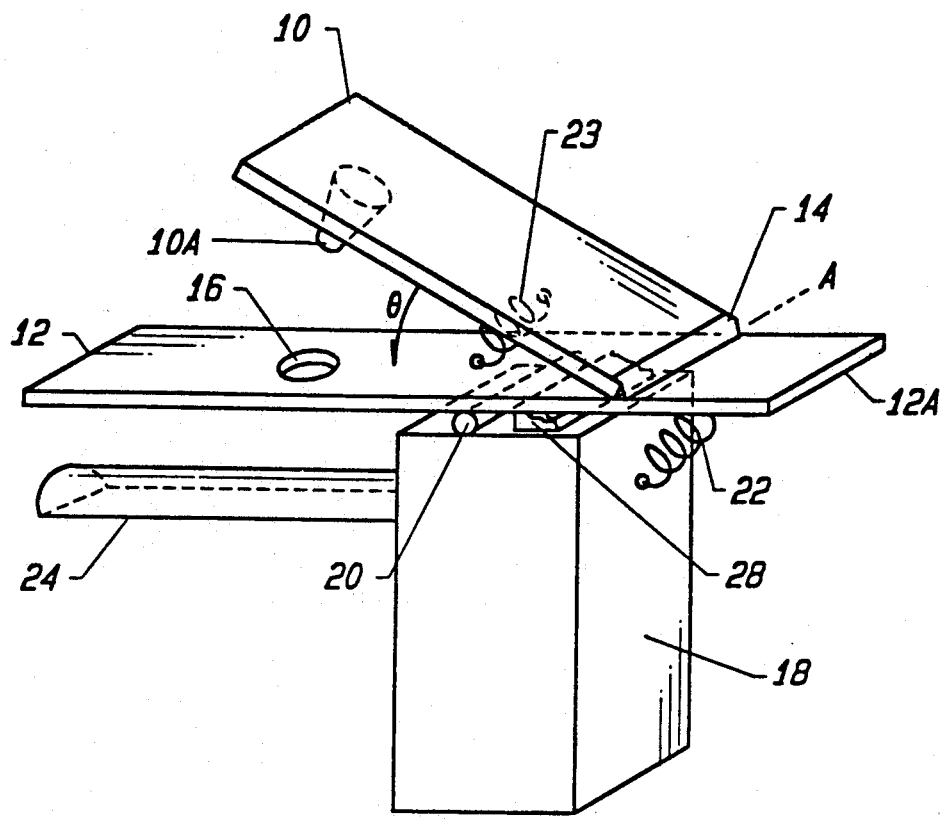
FIG. 1 is a perspective view of a densitometer according to the present invention.

Referring to FIG. 1, a reflection densitometer 10 is flexibly coupled to a base 12 at axis A. Preferably, the coupling at axis A is a hinged receptacle 14 into which the densitometer 10 can be removably placed, thus fixing the planar orientation of the densitometer relative to base 12, but allowing angular movement of the densitometer toward and away from the base.

The base 12 has an opening 16 sized to receive the optical head 10a of the densitometer 10. Thus, when the densitometer 10 is pressed toward the base 12, the optical head 10a is inserted through the opening 16 in order to measure the color quality of the underlying sample.

The base 12 is coupled to a measurement stand 18 via hinge 20. The measurement stand 18 is fixed in position by bolting or otherwise connecting it to a table or other flat surface (not shown). However, the measurement stand 18 could readily be made portable. A first tension spring 22 is attached between the proximate end 12a of the base 12 and the measurement stand 18 to bias the base upwardly. A second tension spring 23 is attached between the base 12 and the densitometer 10. The second spring 23 has a higher coefficient of tension than the first spring 22.

An arcuate shoe or mandrel 24 is rigidly coupled to the measurement stand 18 for supporting a cylindrical sample as further described below.

As noted in the Background section above, reflectometer systems have a specific illumination and measurement geometry by convention. See, for example, ANSI Ph2.17, ISO 5/4, and DIN 16536. It is relatively easy to maintain geometric accuracy when measuring flat samples by prior art methods, for example, by having the sample laid flat on a measurement table which is fixed with respect to the densitometer head. However, since the present invention contemplates the measurement of cylindrical objects, or more generally, rounded surfaces, it is clear that the orientation of the sample relative to the densitometer head must be strictly controlled in order to maintain the proper illumination and measurement geometry. In fact, no matter what type of measurement instrument is used, the orientation of the device relative to the surface to be measured is critical to the success of the present invention.

In the present embodiment, strict control of illumination and measurement geometry may be maintained by constructing the base 12 and shoe 24 in such a way as to ensure that the can will be positively positioned relative to the densitometer head 10. This may be done by having a series of interchangeable base and shoe fittings which correspond to different can sizes and which will hold the can such that the densitometer can be positioned in a fixed radial orientation relative to the surface of the sample.

Figure 2:
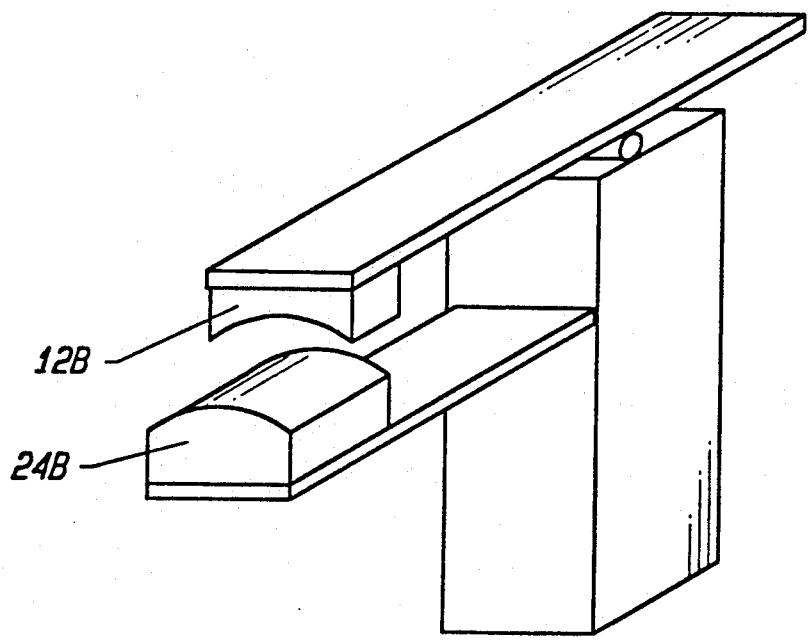
FIG. 2 is a sectional perspective view taken across section 2—2 of FIG. 1.

As shown in FIG. 2, advantageously, a base nip 12b and a shoe nip 24b may be constructed to couple with the base 12 and the shoe 24. Thus, base nip 12b and shoe nip 24b are conveniently constructed as arcuate sections, each with a curvature that corresponds to, and will positively engage, the outside and inside surfaces, respectively, of the can. Thus, each time a can is inserted over the shoe 24, or rotated, the action of pressing down the densitometer head 10 will cause base nip 12b and shoe nip 24b to clamp down on the can, thus locking it into position for measurement.

Figure 3:
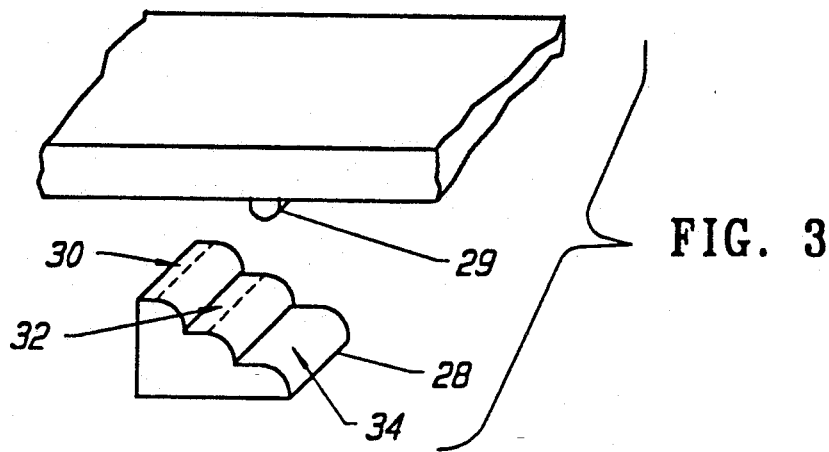
FIG. 3 is a sectional perspective view taken across section 3—3 of FIG. 1.

It can be appreciated that the densitometer 10 and the base 12 are capable of flexure toward the shoe 24, and further, that such flexure must be strictly controlled in order to properly measure the sample. As shown in FIG. 3, this can be accomplished by having a cam 28 integral with the top of the measurement stand 18 for guiding the cam follower 29 which is integral with base 12. The cam 28 is constructed so that the relative angular position of the densitometer 10, the base 12, and the shoe 24 is restricted to three discrete positions, namely an open position, where the cam follower 29 rests on level 30 of cam 28, a clamp position where the cam follower 29 rests on level 32 of cam 28, and a read position. In the open position, no pressure is applied to the densitometer, such that at least 0.25 inches of clearance exists between the base 12 and the shoe 24, thereby allowing insertion of the can over the shoe. It is, of course, possible to increase clearance by exerting downward pressure on the proximate end 12a of the base 12.

As downward pressure is initially applied to the densitometer 10, the cam follower 29 drops to level 32 of cam 28 and the sample can is clamped rigidly in place between the base 12 and the shoe 24. This is the clamp position.

As the densitometer is pressed further downward to the full extent of its angular movement, the cam follower 29 drops to level 34 of cam 28, and the optical head 10a is placed 0.025 inches off the can surface through opening 16 in the proper fixed orientation, i.e., such that the illumination and measurement angles are in accordance with industry standards. This is the read position. A densitometer reading is then taken. Typically, a limit switch is engaged by moving the densitometer to the read position. It is critical that the distance between the densitometer head 12a and the can surface be controlled to within ±0.005 inches in order to maintain the accuracy of the densitometer readings.

In the open position, the can may be rotated and translated to expose different portions of the can surface to the densitometer 10 for a measurement.

Figure 4:
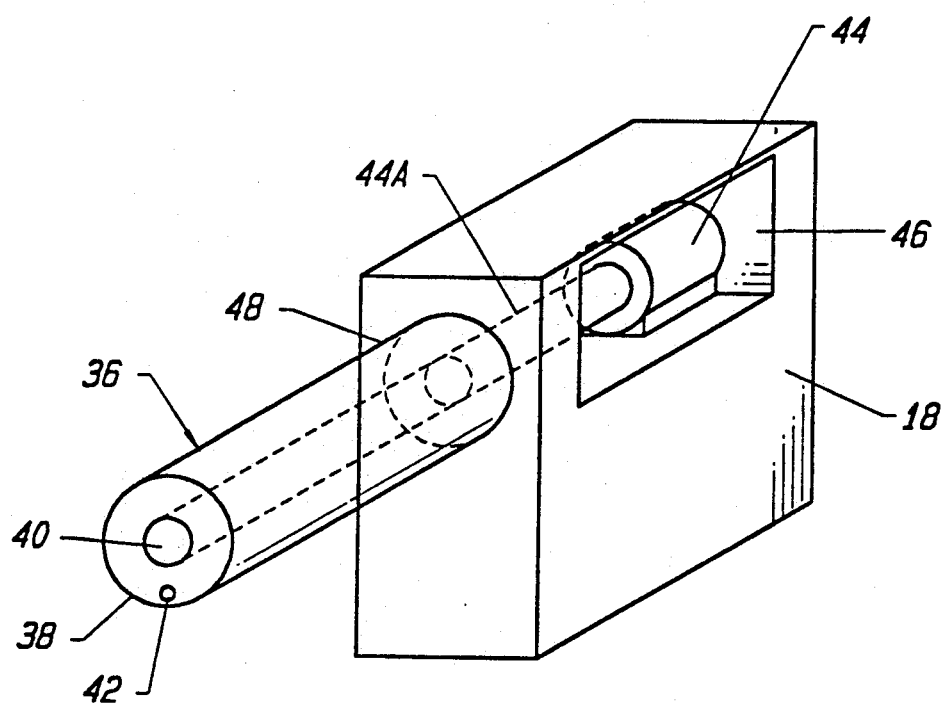
FIG. 4 is a perspective view of an alternative embodiment of a densitometer according to the present invention.

An alternative embodiment is illustrated in FIG. 4. The shoe is replaced by an expandable mandrel 36. The mandrel 36 includes a bladder 38 which is mounted for rotation on an axle 40. An air valve 42 is connected to the bladder 38 for inflating or deflating the bladder. Thus, when a can is inserted over the bladder 38, the bladder may be expanded to firmly grip the interior surface of the can.

The axle 40 is coupled to a motor 44 which may be mounted inside cutout portion 46 in the measurement stand 18. Preferably, a turret assembly 48 coupled the axle 40 to the motor shaft 44a.

The motor 44 is controlled by a conventional personal computer (PC) in order to drive the shaft 44a, and hence the axle 40 to a specific angular position. In this way, densitometer measurements can be taken at a series of predetermined circumferential positions on the can by appropriately programming the PC. Thus, for example, when the densitometer 10 is fully depressed, it can be directed by the PC to take a measurement. The PC then rotates the shaft 44a to the next predetermined position, and the next reading is taken. This method can be repeated as required.

It is, of course, necessary to align a known location on the can with a known angular position of the axle in order to have meaningful densitometer data. This can be done by manually aligning a mark on the can with a mark on the axle. Alternatively, automatic alignment is possible using the method disclosed in the inventors' co-pending U.S. patent application Ser. No. 741,748, entitled "Method and Apparatus for Automatic Densitometer Alignment" and filed Aug. 7, 1991, which is incorporated herein by reference.

Figure 5A:
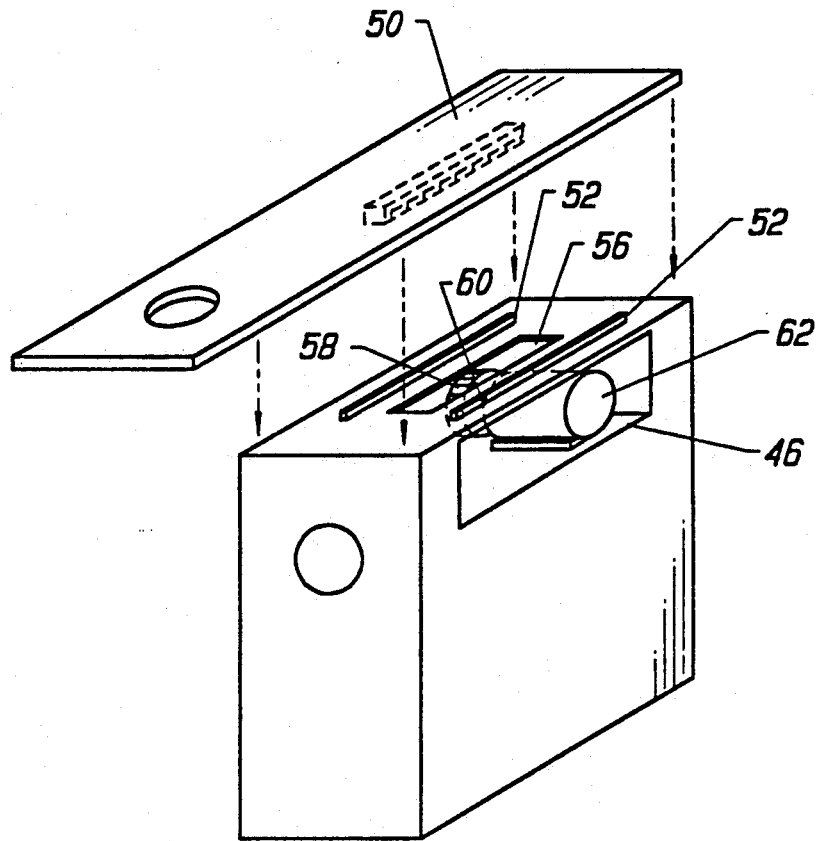
FIG. 5a is a perspective view showing yet another embodiment of a densitometer according to the present invention.
Figure 5B:
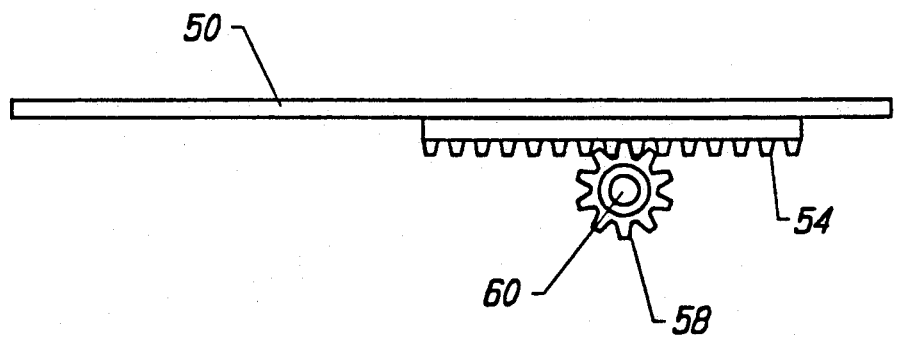

It is preferable to incorporate a scheme for translational control of the densitometer 10 as well. Thus, in FIGS. 5a and 5b, the base 50 is slidably attached to rails 52 on top of the measurement stand 18. The base 50 has a section of teeth 54 which fit through opening 56 in the top of the measurement stand 18. The teeth engage with gear 58. The gear 58 is mounted on shaft 60 of motor 62, which is mounted inside cutout portion 46. As before, the angular position of shaft 60, and hence the translational position of base 12, can be PC controlled. Alignment methods have been previously discussed.

Figure 6A:
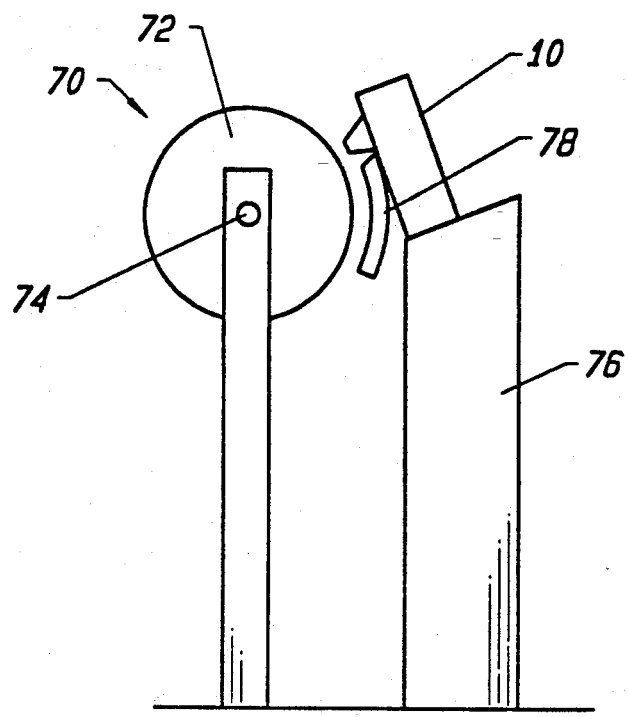
FIGS. 6a and 6b are perspective views showing yet another embodiment of a densitometer according to the present invention.
Figure 6B:
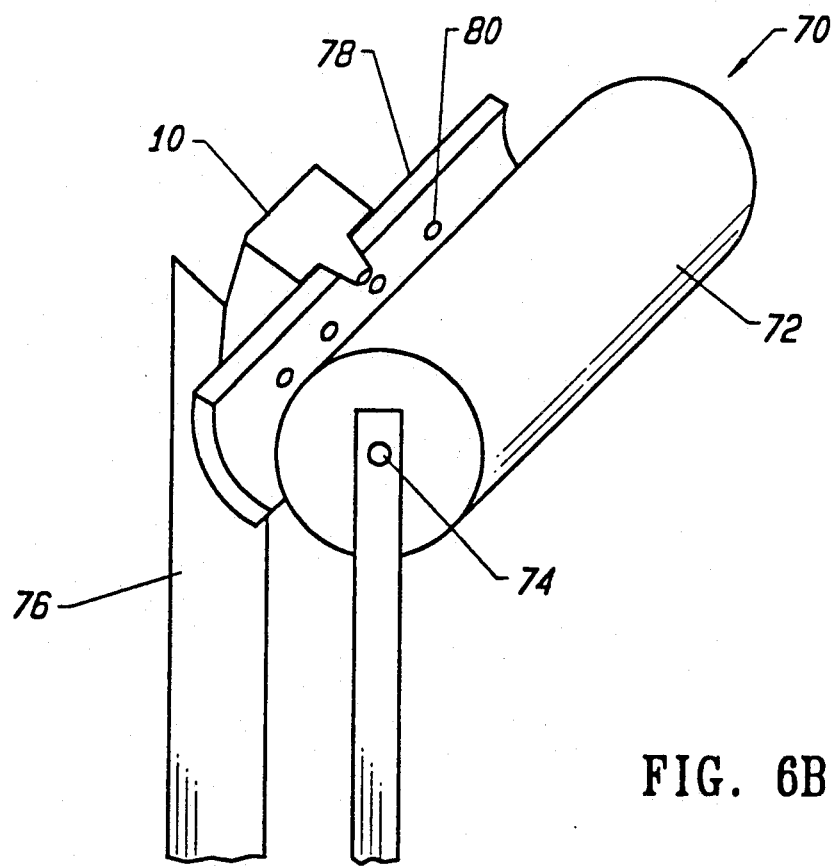

In yet another embodiment, illustrated in FIGS. 6a and 6b, the mandrel 70 includes expandable bladder 72 mounted on axle 74. However, in this embodiment, the axle 74 is free to rotate.

The densitometer 10 is mounted on stand 76 and slidably fitted on the stand for PC control of translational position as previously described.

A manifold 78 is coupled to the densitometer 10. The manifold 78 has a plurality of openings 80 on the side of the manifold which faces the can surface. In one preferred construction, the openings 80 are 0.0625 inches in diameter. An air supply (not shown) provides 2 cfm at 20 psi through the openings 80 to hold a 1 pound densitometer just off the surface of the can. This type of static air bearing is particularly useful to enable the measurement of sample surfaces while the printed matter thereon is still wet.

It should be understood that the invention is not intended to be limited by the specifics of the above-described embodiment, but rather defined by the accompanying claims.

We claim:

1. A method for measuring the color quality of preselected measurement points on a rounded surface having printed matter thereon, comprising:
   a. establishing a measuring device, including a light source and a light detector, in a predefined radial orientation relative to the rounded surface, such that each of the preselected measurement points have a defined rotational and translation relationship relative to the measuring device; and
   b. activating the measuring device, whereby the color quality of each preselected measurement point is obtained via the measuring device.

2. The method of claim 1, wherein the activating step comprises activating a controller which is coupled to the measuring device, said controller moving the measuring device to each of said preselected measurement points and measuring the color quality therof.

3. A system for measuring the color quality of preselected measurement points on a rounded surface having printed matter thereon, comprising:
   a. measuring means for measuring the color quality of the rounded surface, including a light source and a light detector having a known orientation relative to each other;
   b. positioning means for establishing the measuring means in a predetermined radial orientation relative to the rounded surface, such that each preselected measurement point has a defined rotational and translational position relative to the measuring means; and
   c. switch means for activating the measuring means, whereby the color quality of the first measurement point is obtained via the measuring device.

4. The system of claim 3, wherein the positioning means comprises rotator means for rotating the relative positions of the measuring means and the rounded surface.

5. The system of claim 3, wherein the positioning means comprises translator means for translating the relative positions of the measuring means and the rounded surface.

6. The system of claim 3, further comprising:
   a. rotator means for rotating the relative positions of the measuring means and the rounded surface; and
   b. translator means for translating the relative positions of the measuring means and the rounded surface.

7. A reflectometer system for measuring the color quality of preselected measurements points on the rounded surface of an object having printed matter thereon, comprising:
   a. holding means for holding the object; and
   b. a reflectometer coupled to the holding means in a predefined orientation relative to the rounded surface, such that a first preselected measurement point on the rounded surface is defined by a first rotational relationship between the reflectometer and the rounded surface and a first translational relationship between the reflectometer and the rounded surface,
   wherein the object is placed on the holding means and the reflectometer is activated such that the color quality of the first measurement point on the rounded surface is obtained via the reflectometer.

8. The system of claim 7, further comprising clamping means for securing the object between the holding means and the reflectometer.

9. The system of claim 8, wherein the reflectometer is flexibly coupled to the holding means and capable of angular planar movement toward and away from the rounded surface of the object, and wherein at least three discrete angular positions of the reflectometer are defined, namely:
   a. an open position, wherein adequate clearance is provided between the reflectometer and the holding means for putting the object on or off the holding means;
   b. a clamp position, wherein the reflectometer is angled to within approximately 0.025 inches of the rounded surface and the clamping means is engaged; and
   c. a read position, wherein the reflectometer is substantially at the rounded surface,
   wherein the reflectometer is normally biased to the open position, and wherein the reflectometer is activated by flexing it from the clamp position to the read position.

10. The system of claim 7, wherein the holding means comprises a mandrel rotatably coupled to a stand.

11. The system of claim 10, further including first controller means for controlling the rotation of the mandrel.

12. The system of claim 11, wherein the reflectometer is coupled to the holding means via an air bearing comprising a manifold conforming to the shape of the rounded surface and having orifices on one side thereof such that air forced through said orifices establishes said predefined orientation.

13. The system of claim 11, further including translator means coupled to the reflectometer for translating the reflectometer laterally across the object while maintaining said predefined orientation.

14. The system of claim 13, further including second controller means connected to the translator means for controlling the translation of the reflectometer.

15. The system of claim 10, wherein the mandrel comprises an expandable bladder coupled to an axle, said axle being rotatably coupled to the stand.

16. A reflectometer system for measuring the color quality of printed matter on a two piece can, comprising:
   a. a stand;
   b. holding means coupled to the stand for holding the can;
   c. a reflectometer flexibly coupled to the stand in such a way as to permit angular movement of the reflectometer in a fixed plane;
   d. switch means for activating the reflectometer; and
   e. clamping means for securing the can in a fixed location between the holding means and the reflectometer,
   wherein a user places the can on the holding means and flexes the reflectometer toward the can, and wherein said clamping means are engaged as the reflectometer nears the can, and wherein said switch means are engaged when said clamping means have been engaged, thus activating the reflectometer in order to take a measurement of the color quality of a preselected point on the surface of the can.

17. The system of claim 16, wherein the holding means comprises a mandrel rotatably coupled to the stand.

18. The system of claim 17, wherein the mandrel comprises an expandable bladder coupled to an axle, said axle being rotatably coupled to the stand.

19. The system of claim 18, further including first controller means for controlling the rotation of the mandrel.

20. The system of claim 19, further including translation means for translating the reflectometer laterally across the can so as to maintain the angular position of the reflectometer relative to the surface of the can.

21. The system of claim 20, further including second controller means for controlling the translation means.

22. The system of claim 20, wherein the holding means comprises a mandrel coupled to the stand.

23. The system of claim 21, wherein the mandrel comprises an expandable bladder.

24. A reflectometer system for measuring the color quality of printed matter on a two piece can, comprising:
   a. a stand;
   b. holding means coupled to the stand for holding the can;
   c. a reflectometer movably coupled to the holding means in a redefined orientation relative to the surface of the can; and
   d. an air bearing coupled to the reflectometer, comprising a manifold conforming to the shape of the can and having openings on one side thereof such that air forced through said openings holds the reflectometer off the surface of the can and establishes said predefined orientation,
   wherein the can is placed on the holding means and the reflectometer is activated so that a color quality measurement at a first measurement point on the surface of the can is obtained, and wherein different measurement points may be measured by translating and/or rotating the reflectometer relative to the can surface, said air bearing maintaining said predefined orientation between the reflectometer and the can surface.

25. The system of claim 24, further comprising:
   a. rotator means for establishing a different rotational relationship between the reflectometer and the surface of the can; and
   b. translator means for establishing a different translational relationship between the reflectometer and the surface of the can.

26. The system of claim 25, further including first controller means for controlling the rotator means.

27. The system of claim 25, further including second controller means for controlling the translator means.

* * * * *